US00PP32584P2

(12) United States Plant Patent
Dirr

(10) Patent No.: US PP32,584 P2
(45) Date of Patent: Dec. 8, 2020

(54) ***HYDRANGEA* PLANT NAMED 'COF-HM3'**

(50) Latin Name: *Hydrangea macrophylla*
Varietal Denomination: COF-HM3

(71) Applicant: Michael Dirr, Bogart, GA (US)

(72) Inventor: Michael Dirr, Bogart, GA (US)

( * ) Notice: Subject to any disclaimer, the term of this patent is extended or adjusted under 35 U.S.C. 154(b) by 0 days.

(21) Appl. No.: 16/602,718

(22) Filed: Nov. 26, 2019

(51) Int. Cl.
*A01H 5/02* (2018.01)
*A01H 6/48* (2018.01)

(52) U.S. Cl.
USPC ..... Plt./250

(58) Field of Classification Search
USPC ..... Plt./227, 250, 226
See application file for complete search history.

*Primary Examiner* — Susan McCormick Ewoldt
*Assistant Examiner* — Karen M Redden
(74) *Attorney, Agent, or Firm* — Cassandra Bright

(57) ABSTRACT

A new and distinct cultivar of *Hydrangea* plant named 'COF-HM3' is disclosed, characterized by vigorously growing, plants exhibiting strong and rapid (8 to 9 weeks) reblooming. Inflorescences are mophead with either medium pink flowers (standard treatment) or violet colored flowers (aluminum sulfate treatment). Plants are cold hardy to USDA Zone 4 and exhibit disease resistance. The new variety is a *Hydrangea*, normally produced as an ornamental plant.

6 Drawing Sheets

Latin name of the genus and species: *Hydrangea macrophylla.*

Variety denomination: 'COF-HM3'.

BACKGROUND OF THE INVENTION

The new *Hydrangea* cultivar was found and selected as a naturally occurring mop head sport of *Hydrangea* 'Twist-n-Shout', U.S. Plant Pat. No. 20,176, in a cultivated garden setting in Storrs, Conn., in July of 2017.

Asexual reproduction of the new cultivar 'COF-HM3' by vegetative soft wood cuttings was first performed during July of 2017, at a commercial greenhouse in Watkinsville, Ga. Subsequent propagation has shown that the unique features of this cultivar are stable and reproduced true to type in successive generations.

SUMMARY OF THE INVENTION

The cultivar 'COF-HM3' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'COF-HM3' These characteristics in combination distinguish 'COF-HM3' as a new and distinct *Hydrangea* cultivar:

1. The mop head inflorescence.
2. Highly vigorous plants.
3. Strong and rapid reblooming occurring in approximately 8 to 9 weeks after cut back. Typical reblooming of commercial varieties is approximately 12 weeks.
4. Cold hardiness, growing in USDA zones 4 through 9.
5. High disease resistance.
6. Medium pink flowers with standard treatment, violet colored flowers with typical commercial aluminum sulfate treatment.

PARENTAL COMPARISON

Plants of the new cultivar 'COF-HM3' is similar to the parent variety *Hydrangea macrophylla* 'Twist and Shout', U.S. Plant Pat. No. 20,176 in most horticultural characteristics. However, 'COF-HM3' differs in the following:

1. The new variety has a mop head inflorescence, the parent has a lace cap inflorescence. DNA markers proved this single difference.

COMMERCIAL COMPARISON

Plants of the new cultivar 'COF-HM3' can be compared to the variety *Hydrangea macrophylla* 'Bailmer', U.S. Plant Pat. No. 15,298. These varieties are similar in most horticultural characteristics; however, 'COF-HM3' differs in the following when produced under identical trial conditions and measured at the same age:

1. The new variety grows approximately 30% faster than this comparator.
2. The new variety produces approximately 30% more flower buds than this comparator.
3. The new variety produces sepals colored darker pink than sepals of this comparator.
4. The new variety produces approximately 20% more inflorescences than this comparator.

Plants of the new cultivar 'COF-HM3' can be compared to the variety *Hydrangea macrophylla* 'Bishop', unpatented. These varieties are similar in most horticultural characteristics; however, 'COF-HM3' differs in the following when produced under identical trial conditions and measured at the same age:

1. The new variety grows approximately 20% faster than this comparator.
2. The new variety produces approximately 30% more flower buds than this comparator.
3. Under low pH conditions, with typical commercial aluminum sulfate treatment, the new variety produces sepals colored violet, compared to the blue sepals of this comparator.

BRIEF DESCRIPTION OF THE PHOTOGRAPHS

'COF-HM3' is illustrated by the accompanying photographs which show the plant's form, foliage, and inflorescences. The colors shown are as true as can be reasonably obtained by conventional photographic procedures. Colors in the photographs may differ slightly from the color values cited in the detailed botanical description, which accurately describe the colors of the new *Hydrangea*. The accompanying photograph in FIG. 1 illustrates in full color a typical inflorescence of 'COF-HM3' in the emerging stage, having no aluminum treatment. FIG. 2 illustrates a typical inflorescence of 'COF-HM3' in the mature stage, having no aluminum treatment. FIG. 3 illustrates an inflorescence in the transitional stage between immature and mature, given a typical aluminum sulfate treatment of 70 grams top dressed. FIG. 4 illustrates the increased growth rate of the new variety. The plant of the left of the figure is the new variety, the row of plants on the right of the figure is the comparator 'Bailmer'. Plants illustrated in FIG. 5 are the same age and cultivated under identical growing conditions. FIG. 6 illustrates plants of the new variety during Fall, with the distinctive Fall foliage coloration.

Figure 1:
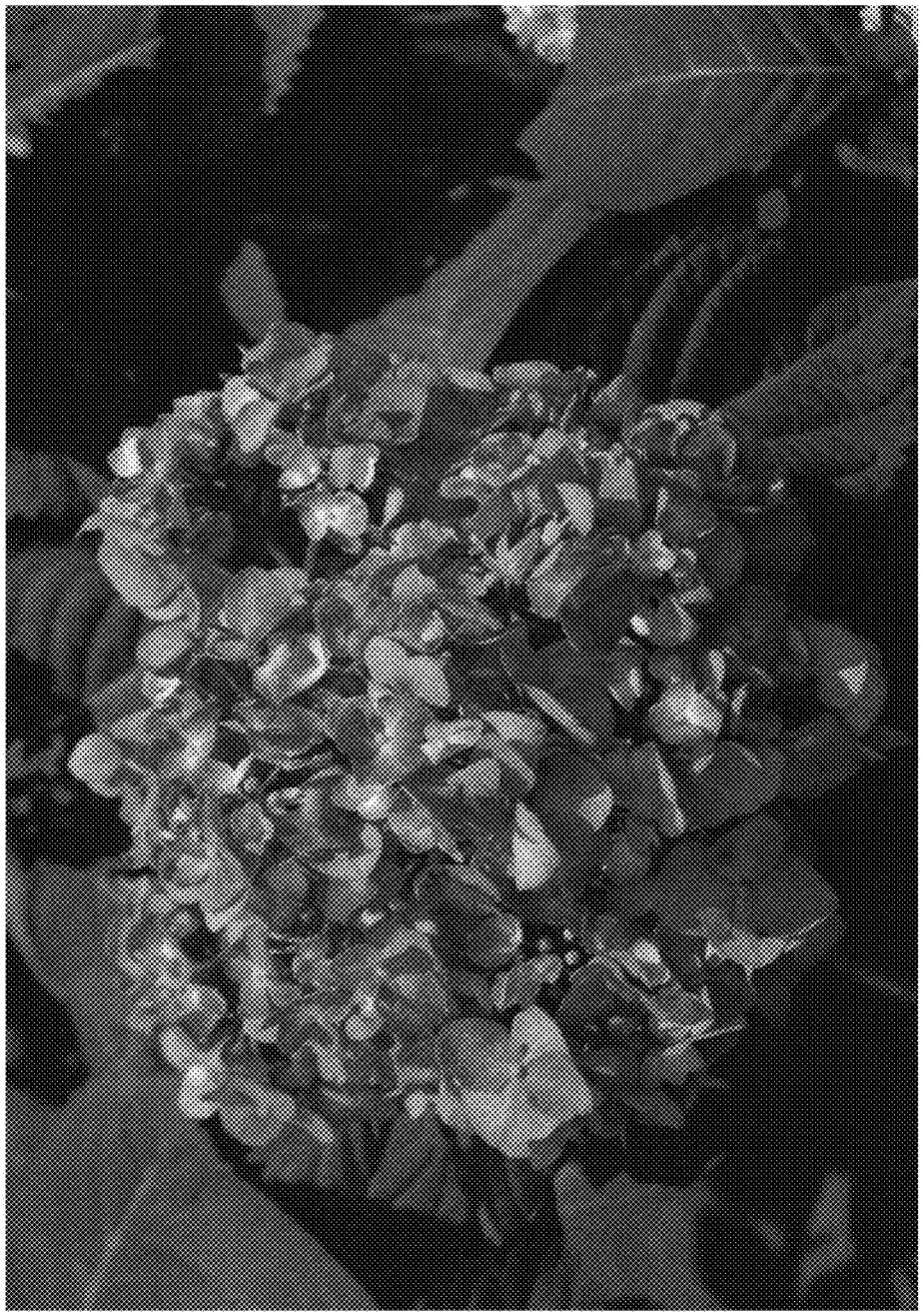
FIG. 1 shows a close-up view of the mature inflorescence during Summer given a typical commercial aluminum treatment to cause bluing.
Figure 2:
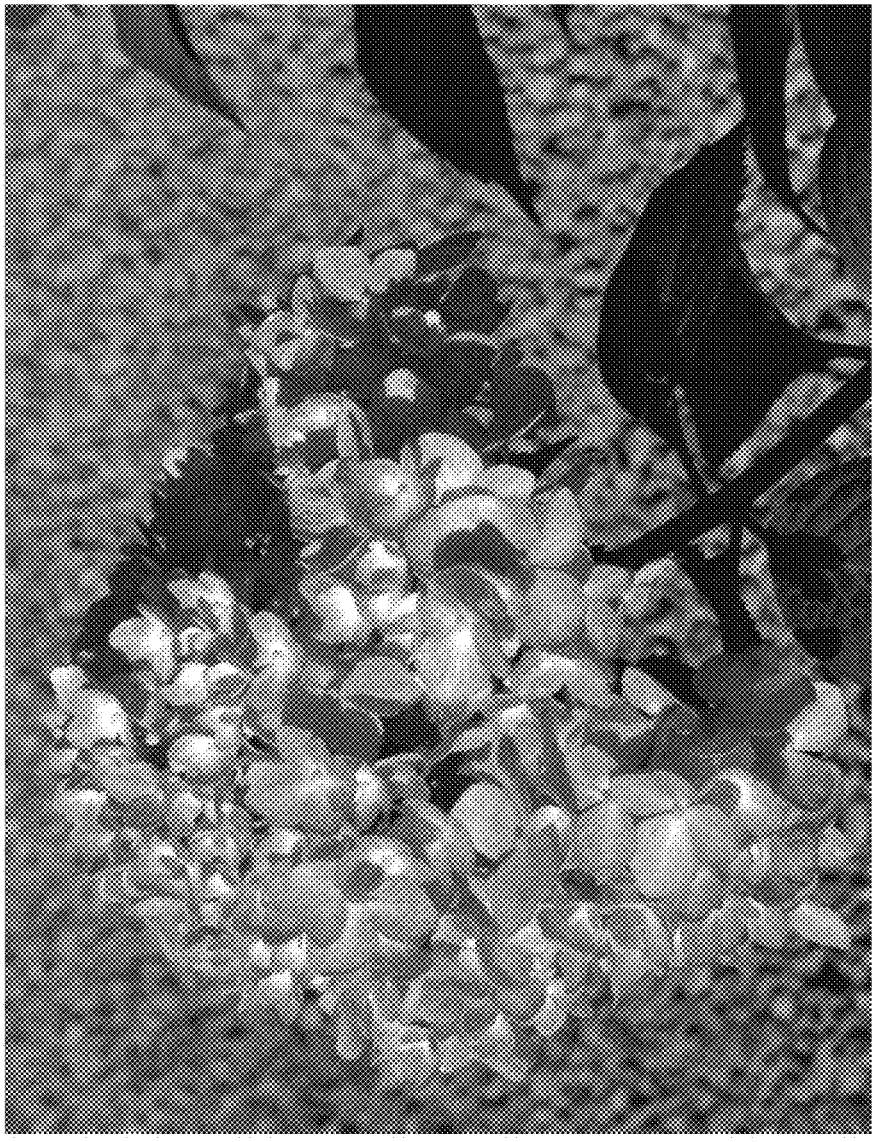
FIG. 2 shows a close-up view of the mature inflorescence during Summer on a plant not given aluminum treatment.
Figure 3:
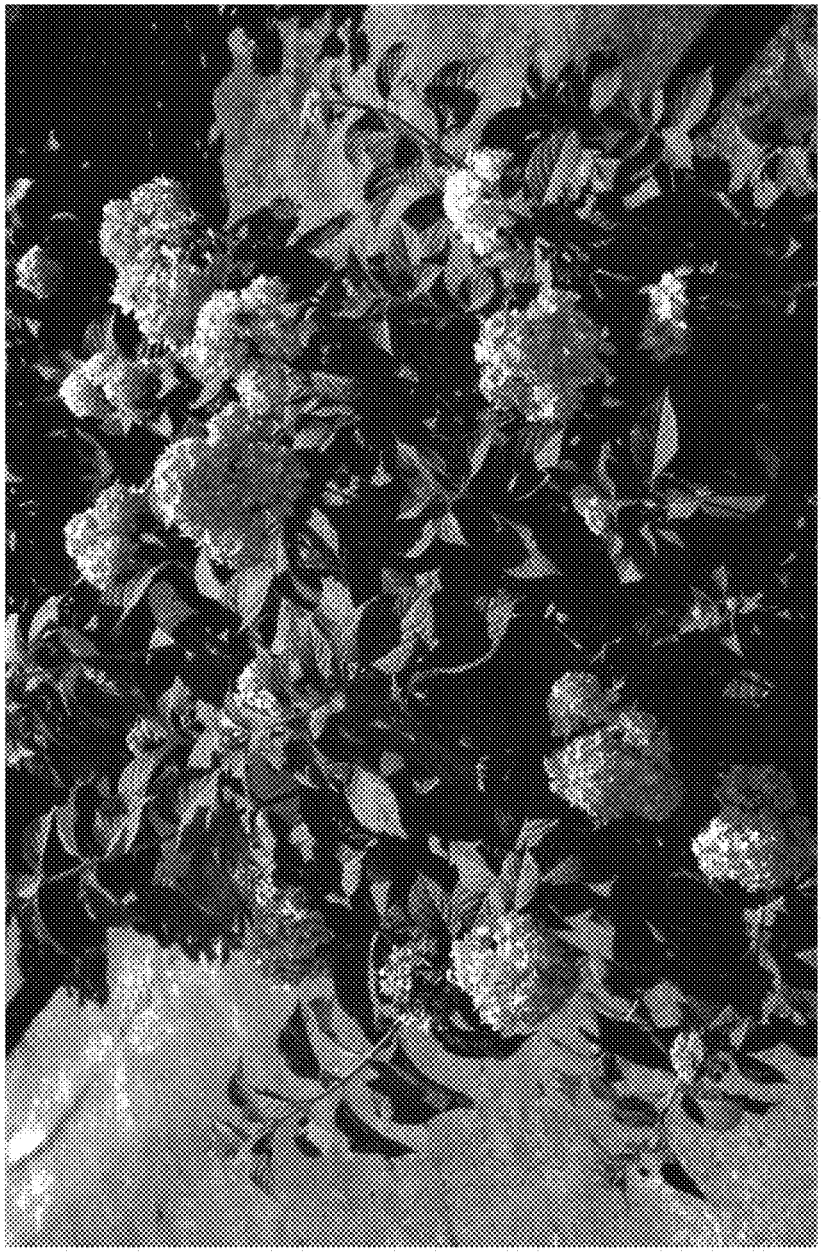
FIG. 3 illustrates in full color a typical plant of 'COF-HM3' in a 10 gallon pot, having no aluminum treatment, with multiple inflorescences at various stages of maturity. The plant in the photograph is approximately 18 months old, in a 10-gallon pot.
Figure 4:
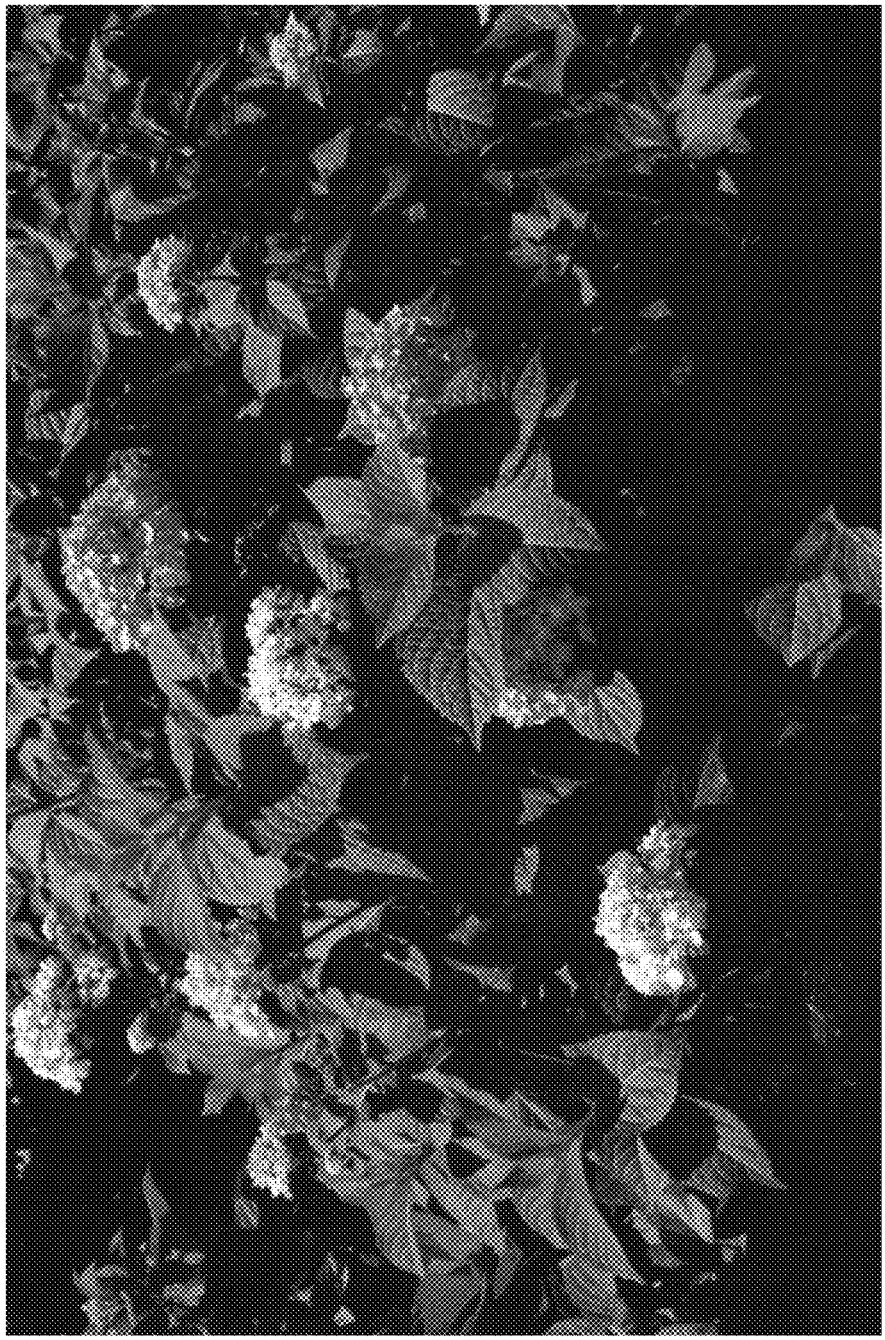
FIG. 4 illustrates reblooming characteristics of 'COF-HM3'. The plant illustrated in a 10 has been cut back during Summer and is illustrated at approximately 9 weeks after the cut back.
Figure 5:
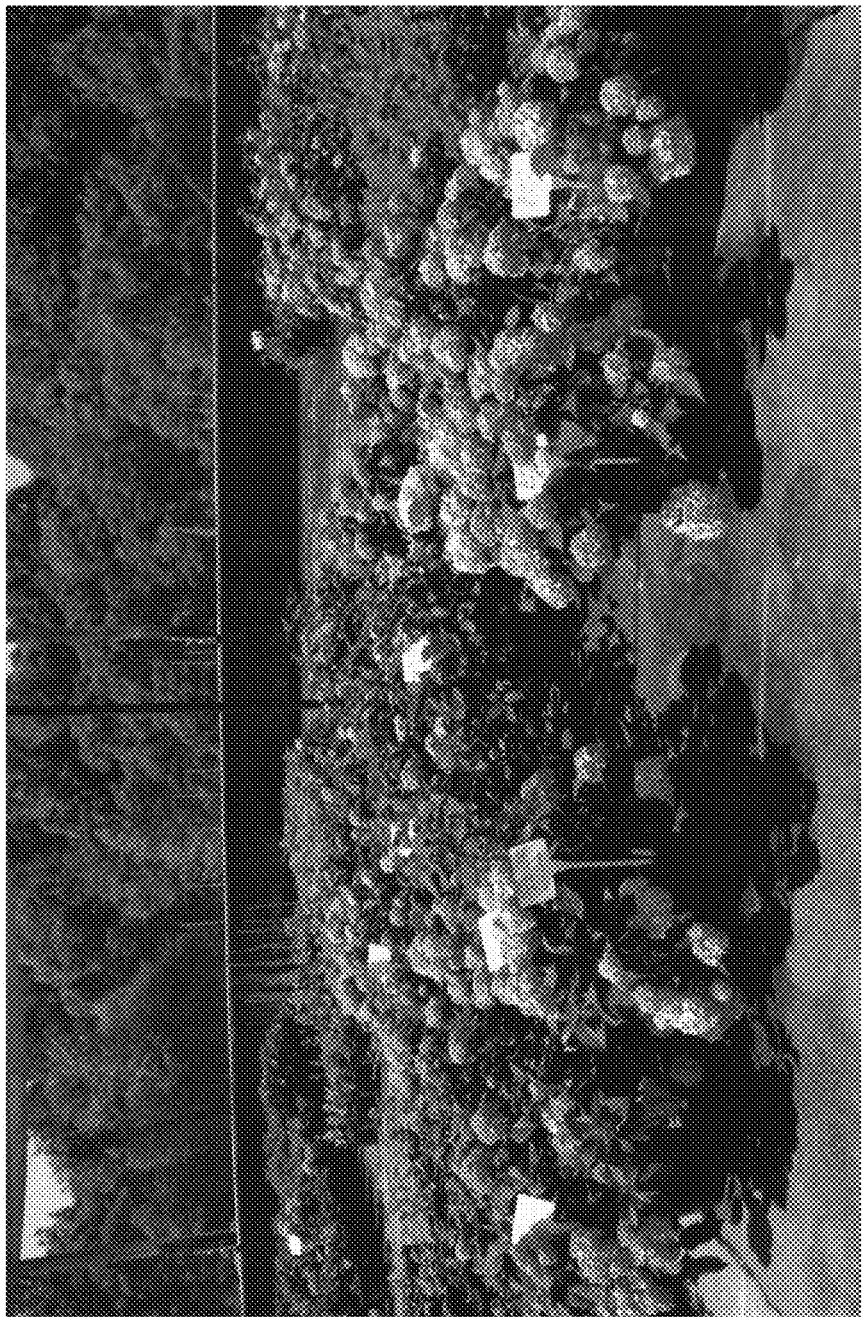

FIG. 5 illustrates a comparative trial. Plants of the new variety are illustrated on the left side of the photograph. The non-flowering plants in the center are the unpatented variety 'Lady in Red'. The flowering plants on the right of the photo are the comparator 'Bishop'.

Figure 6:
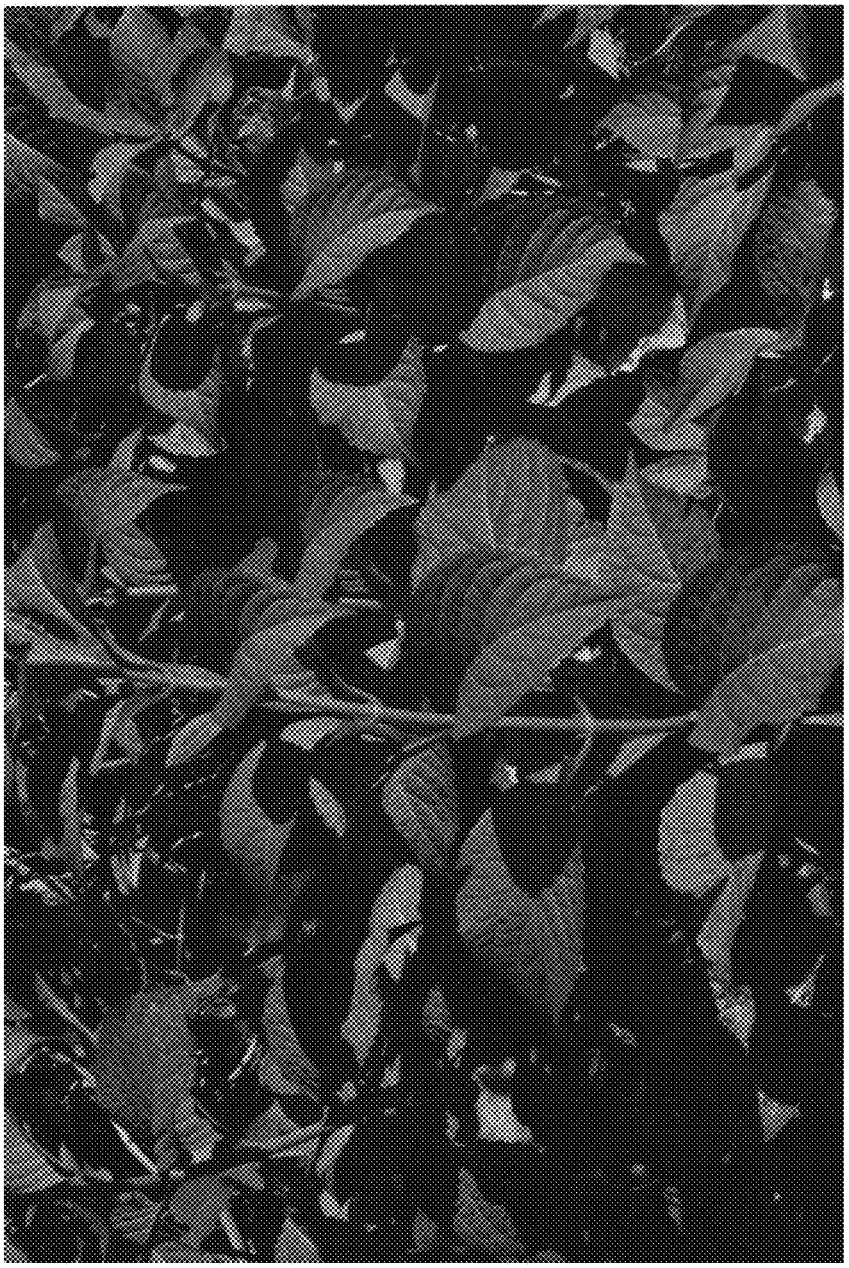

FIG. 6 illustrates Fall foliage color of 'COF-HM3'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'COF-HM3' plants grown in a commercial greenhouse in Watkinsville, Ga., outdoors under 50% saran shade. Measurements were taken during June of 2019. The plants were about 18 months old planted in 10-gallon pots. The growing temperature ranged from 20° C. to 30° C. during the day, and 10C.° to 25° C. at night. Measurements and numerical values represent averages of typical plant types.

Botanical classification: *Hydrangea macrophylla* 'COF-HM3'.

PROPAGATION

Age of plant described: Approximately 12 months from a rooted cutting.

Time to rooting: 21 to 28 days at approximately 20° to 25° C.

Root description: Profuse, diffuse, well branched, RHS White 155D.

PLANT

Growth habit: Rounded to broad-rounded, more vigorous than other remontant cultivars, and with a more open constitution at flowering maturity.

Overall plant shape: Rounded.

Height: Approximately 90 cm.

Plant spread: Approximately 90 cm.

Growth rate: Rapid.

Branching characteristics:

Length of lateral branches/stems: Approximately 50 cm.

Number of lateral branches: Approximately 30.

Diameter of lateral branches: Approximately 0.5 cm.

Pinching required: Yes. Twice, remove top two nodes.

Lateral branch shape: Round.

Lateral branch strength: Moderate.

Lateral branch/stem color: RHS Greyed-Yellow 199C.

Branch angle: 30° to 40°.

Other stem or plant characteristics:

*Lenticel length.*—Approximately 2 mm.

*Lenticel width.*—Approximately 0.5 mm.

*Lenticel color.*—Near RHS Greyed-Orange 176D.

Number of leaves per lateral branch: Average 20.

FOLIAGE

Leaf:

*Arrangement.*—Opposite.

*Compound or single.*—Single (simple leaf).

*Average length.*—Approximately 12 cm.

*Average width.*—Approximately 6 cm.

*Shape of blade.*—Ovate.

*Lobing.*—None.

*Apex.*—Short acuminate.

*Base.*—Rounded.

*Attachment.*—With petiole.

*Margin.*—Serrate.

*Texture of top surface.*—Rough, veins deeply impressed.

*Texture of bottom surface.*—Rough, veins raised above lower surface.

*Leaf internode length.*—Approximately 5 cm.

*Color.*—Young foliage upper side: Near RHS Green 139A. Young foliage under side: Near RHS Green 139B. Mature foliage upper side: Near RHS Green 139A. Mature foliage under side: Near RHS Green 139C. Fall foliage upper side: Near RHS Greyed-Purple 185B with some flushing near Greyed-Purple 187A. Fall foliage under side: Near RHS Greyed-Purple 185B flushed Red 45B.

*Venation.*—Type: Pinnate with deeply impressed veins. Venation color upper side: Near RHS Greyed-Purple 183C. Venation color under side: Near RHS Green 139D.

*Durability of foliage to stresses.*—Moderate.

Petiole:
*Average length*.—Approximately 1.5 cm.
*Diameter*.—Approximately 3 mm.
*Texture*.—Stout, firm.
*Color*.—Near RHS Greyed-Purple 183C.

FLOWER

Bloom period:
*Natural season*.—May to June, continuously flowering on new growth until October.
*Flowering continuous, sporadic, intermittent, or other*.—Continuous (remontant on new growth).
Inflorescence:
*Type*.—Corymb.
*Arrangement*.—Freely branched mop head -borne terminally at end of shoots.
*Shape*.—Rounded globose.
*Height*.—Approximately 9 cm.
*Width*.—Approximately 17 cm.
*Quantity of flowers per inflorescence*.—Fertile flowers: Approximately 72. Sterile Flowers: Approximately 130.
Sterile Flower:
Bud:
*Bud shape*.—Round.
*Bud length*.—Approximately 1.5 mm.
*Bud diameter*.—Approximately 1.5 mm.
*Bud color*.—Near RHS Greyed-Orange 174C.
*Base/calyx*.—Near RHS Greyed-Orange 174C.
Sterile flowers: Not observed open.
Sterile flower sepal:
*Arrangement*.—Clustered on pedicel.
*Number*.—4.
*Shape*.—Ovate to broad ovate.
*Tip*.—Abrupt.
*Base*.—Broad cuneate to rounded.
*Margin*.—Entire.
*Length*.—1.7 cm.
*Width*.—1.7 cm.
*Texture, upper*.—Fine.
*Texture, lower*.—Fine.
*Color*.—Upper surface at first opening: Acidic: Near RHS Violet-Blue 96D. Basic: Near RHS Red-Purple N66D. Upper surface at maturity: Acidic: Near RHS Violet-Blue 96D. Basic: Near RHS Red-Purple 67B. Under surface at first opening: Acidic: Near RHS Violet-Blue 97A. Basic: Near RHS Red-Purple 68C. Under surface at maturity: Acidic: Near RHS Violet-Blue 98D. Basic: Near RHS Red-Purple 68A. Fading to Upper surface: Acidic: Near RHS Violet-Blue 96B. Basic: Near RHS Red-Purple 68A. Fading to Under surface: Acidic: Near RHS Violet-Blue 96C. Basic: Near RHS Red-Purple 68C.
Sterile flower pedicel:
*Length*.—1.5 cm.
*Diameter*.—1 mm.
*Angle*.—25°.
*Strength*.—Flimsy.
*Texture*.—Fine.
*Color*.—Acidic: Near RHS Violet 92A. Basic: Near RHS Red-Purple N74B.
Petaloids: Not present.
Fertile flower: This is flower under the sepals and which I use for breeding as it carries fertile anthers and pistils.
*Bud shape*.—Rounded with five suture lines.
*Bud length*.—2 mm.
*Bud diameter*.—3 mm.
*Bud color*.—Acidic: Near RHS Violet-Blue 95C. Basic: Near RHS Red-Purple N74C.
*Flower aspect*.—Not showy.
*Flower shape*.—Star-shaped.
*Flower length*.—3 mm.
*Flower diameter*.—6 mm.
*Flower depth*.—2 mm.
*Self-cleaning/persistent*.—Self-cleaning.
Fertile flower petals:
*Length of petal*.—2 mm.
*Width of petal*.—1.5 mm.
*Apex*.—Abrupt.
*Shape of petal*.—Linear-ovate.
*Petal margin*.—Entire.
*Petal arrangement*.—Actinomorphic.
*Petal number*.—5.
*Petal base*.—Cuneate.
*Petals fused*.—Free.
*Petal texture*.—Fine.
*Color*.—Upper surface at first opening: Acidic: Near RHS Violet 92B. Basic: Near RHS Red-Purple N74D. Upper surface at maturity: Acidic: Near RHS Violet 92A. Basic: Near RHS Red-Purple N74C. Under surface at first opening: Acidic: Near RHS Violet 91B. Basic: Near RHS Red-Purple N74D. Under surface at maturity: Acidic: Near RHS Violet-Blue 97A. Basic: Near RHS Red-Purple N74C. Upper surface fading to: Acidic: Near RHS Violet-Blue 98B. Basic: Near RHS Red-Purple N74C. Lower surface fading to: Acidic: Near RHS Violet-Blue 98C. Basic: Near RHS Red-Purple N74D.
Fertile flower sepal:
*Arrangement*.—Solitary.
*Number*.—5.
*Shape*.—Star-shaped.
*Tip*.—Acute.
*Base*.—Truncate.
*Margin*.—Entire.
*Length*.—1 mm.
*Width*.—1.5 mm.
*Texture, upper*.—Fine.
*Texture, lower*.—Fine.
*Color*.—Upper surface at first opening: Near RHS Red-Purple N74C. Upper surface at maturity: Near RHS Red-Purple N74C. Under surface at first opening: Near RHS Red-Purple N74C. Under surface at maturity: Near RHS Red-Purple N74C. Upper surface fading to: Near RHS Red-Purple N74C. Lower surface fading to: Near RHS Red-Purple N74C.
Fertile flower pedicel:
*Angle*.—30°.
*Strength*.—Moderate.
*Length*.—4 mm.
*Width*.—Less than 1 mm.
*Texture*.—Fine.
*Color, same basic or acidic*.—Near RHS Red-Purple N74C.
Peduncle:
*Length*.—Approximately 5 cm.
*Diameter*.—Approximately 2.5 mm.
*Texture*.—Moderate.
*Angle*.—70°.
*Strength*.—Strong enough to hold sepals upright.
*Color*.—Near Green 138C.

REPRODUCTIVE ORGANS

Sterile flower: Not observed.

Fertile flower:

*Stamen number.*—10.

*Filament length.*—3 mm.

*Filament color.*—Near RHS Red-Purple 73B.

*Anther shape.*—Oblong.

*Anther length.*—1 mm.

*Anther color.*—Near RHS Red-Purple 73B.

*Pollen amount.*—Present but minimal.

*Pollen color.*—Near RHS White 155B.

Gynoecium:

*Pistil number.*—1.

*Pistil length.*—4 mm.

*Stigma shape.*—3-lobed.

*Stigma color.*—Near RHS Red-Purple 73A.

*Style length.*—Less than 1 mm.

*Style color.*—Near RHS Red-Purple 73A.

*Ovary color.*—Near RHS Red-Purple 73A.

OTHER CHARACTERISTICS

Disease resistance: High resistance to powdery mildew. Moderate to high resistance to cercospora *Hydrangea* which devastates the legacy French/European hybrids as well as the original remontant *Hydrangea* like 'Bailmer', U.S. Plant Pat. No. 15,298, 'David Ramsey' (unpatented), 'Decatur Blue' (unpatented), 'Oak Hill' (unpatented), and 'Penny Mac' (unpatented).

Drought tolerance and cold tolerance/temperature range: USDA Zones 4 through 9.

Fruit/seed production: Minimal. Fruit capsules are formed. Most abort. Capsule is smooth (unribbed), avoid, about 7 mm long and 3 mm wide. Colored near Yellow-Green 144A.

What is claimed is:

1. A new and distinct cultivar of *Hydrangea* plant named 'COF-HM3' as herein illustrated and described.

* * * * *